(12) United States Patent
Patel

(10) Patent No.: US 12,201,733 B2
(45) Date of Patent: Jan. 21, 2025

(54) TRANSDERMAL DELIVERY SYSTEM

(71) Applicant: Nikita Patel, Sinking Spring, PA (US)

(72) Inventor: Nikita Patel, Sinking Spring, PA (US)

( * ) Notice: Subject to any disclaimer, the term of this patent is extended or adjusted under 35 U.S.C. 154(b) by 163 days.

(21) Appl. No.: 17/685,818

(22) Filed: Mar. 3, 2022

(65) Prior Publication Data
US 2022/0280443 A1 Sep. 8, 2022

Related U.S. Application Data

(60) Provisional application No. 63/158,036, filed on Mar. 8, 2021.

(51) Int. Cl.
*A61K 9/70* (2006.01)
*A61K 31/485* (2006.01)

(52) U.S. Cl.
CPC .......... *A61K 9/7092* (2013.01); *A61K 9/7084* (2013.01); *A61K 31/485* (2013.01)

(58) Field of Classification Search
None
See application file for complete search history.

(56) References Cited

U.S. PATENT DOCUMENTS 4,573,996 A * 3/1986 Kwiatek .............. A61K 9/7084
424/448
5,972,384 A * 10/1999 Thut ..................... C03C 4/0007
424/484

FOREIGN PATENT DOCUMENTS

CA 2652216 A1 * 12/2007 ........... A61K 9/7069

OTHER PUBLICATIONS

Huang et al. (Bioactive glass as nanoporpus drug delivery system for teicoplanin), Applied Science, 10, 2595 (Year: 2020).*
Jiang et al. (Polymer microneedles integrated with glucose-responsive mesoporous bioactive glass nanoparticles for transdermal delivery of insulin), Biomedical Physics & Engineering Express 5, 045038 (Year: 2019).*

* cited by examiner

*Primary Examiner* — Isis A Ghali
(74) *Attorney, Agent, or Firm* — Brennan, Manna & Diamond, LLC

(57) ABSTRACT

A system for the transdermal delivery of drugs, vitamins, or micronutrients over a time interval of up to one month. The transdermal delivery system employs a plurality of varying diameter bioactive glass capsules configured to react with water in the bloodstream to break down and release a contained dose of a drug, vitamin, or other micronutrients. The bioactive glass capsules are microscopic and able to be absorbed through the skin. An adhesive bandage is adhered to the skin via an adhesive layer. A concealed membrane is positioned centrally on an inner surface of the adhesive bandage and separated by a barrier layer. The bioactive glass capsules are housed within the concealed membrane until the patch is placed on the skin allowing them to absorb through the skin to deliver up to a month's dose of the drug, vitamin, or other micronutrients into the bloodstream.

2 Claims, 4 Drawing Sheets

TRANSDERMAL DELIVERY SYSTEM

CROSS-REFERENCE TO RELATED APPLICATION

Figure 1:
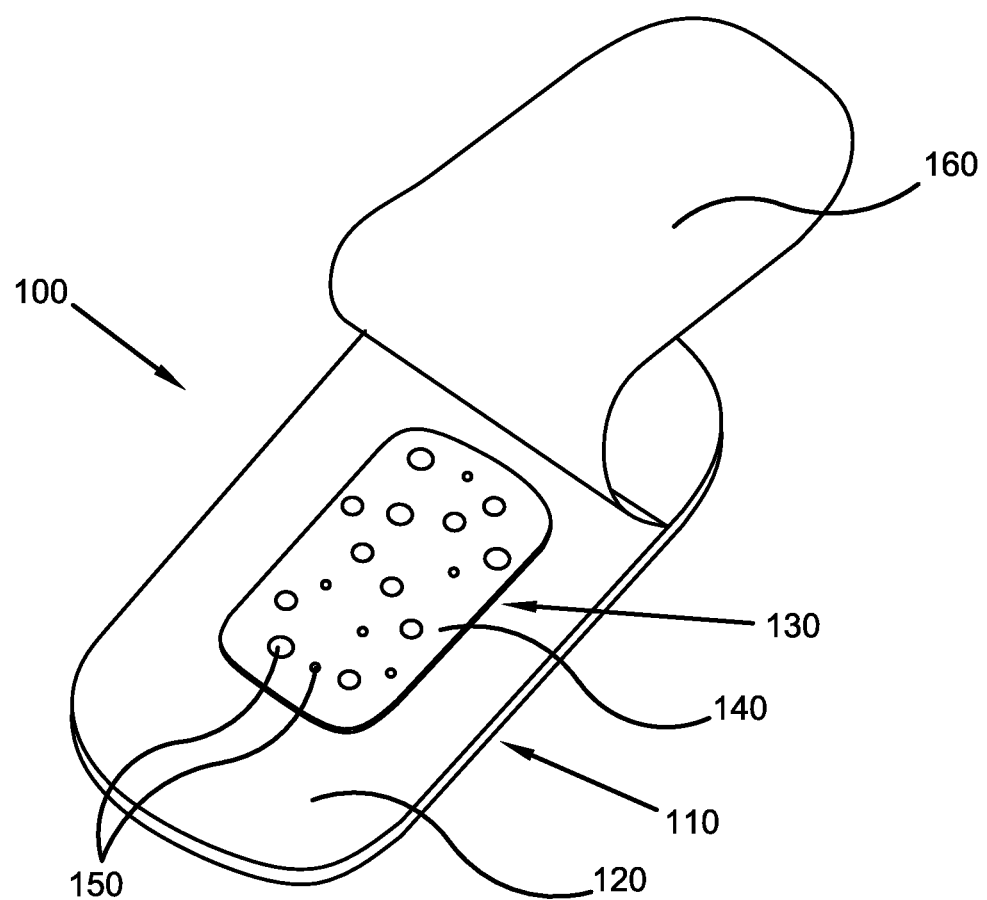

The present application claims priority to, and the benefit of, U.S. Provisional Application No. 63/158,036, which was filed on Mar. 8, 2021 and is incorporated herein by reference in its entirety.

FIELD OF THE INVENTION

The present invention generally relates to a needleless transdermal delivery system, and more specifically to a transdermal system for delivering time-released drugs, vitamins, and micronutrients through the skin. Accordingly, the present specification makes specific reference thereto. However, it is to be appreciated that aspects of the present invention are also equally amenable to other like applications, devices, and methods of manufacture.

BACKGROUND

Transdermal medication patches cannot be used in many drug delivery settings because there is often no way to encase the medication from the skin. This is bad because some forms of medication cannot directly touch skin because of toxicity levels, therefore limiting the uses of transdermal patches. Another problem with transdermal patches is that they are inconvenient to put on every day for the prescribed period of time. This may make it more convenient to choose an oral administration option. Unfortunately, daily medications are often accidently forgotten limiting the medication effectiveness.

Transdermal is a route of administration where active ingredients are delivered across the skin for systemic distribution. Examples that use this method include transdermal patches used for medicine delivery. The drug is administered in the form of a patch or ointment that is positional on the skin for several hours to deliver the drug through the skin and into the circulation for systemic effect. Although the skin is a large and logical target for drug delivery, its basic functions limit its utility for this purpose. The skin functions mainly to protect the body from external penetration by foreign substances and microorganisms. For transdermal delivery, drugs must pass through both sublayers of the epidermis to reach the microcirculation of the dermis.

The stratum corneum is the outer most layer of the epidermis and varies in thickness from approximately ten to several hundred micrometers depending on the location of the body. This layer is the most significant barrier to diffusion through the skin. In fact, the stratum corneum is the barrier to approximately 90% of transdermal drug applications. However, nearly all molecules penetrate it at least to some minimal degree. The viable epidermis is directly below the stratum corneum. This layer is about ten times as thick as the stratum corneum. However, diffusion is much faster in this layer due to the greater degree of hydration in the living cells of the viable epidermis. The dermis is directly below the epidermis, which is approximately one millimeter thick. The dermis contains small vessels that distribute drugs into the systemic circulation and to regulate temperature, a system known as the skin's microcirculation.

A transdermal patch is a medicated adhesive patch that is positioned directly on the skin to non-invasively deliver a specific dose of medication through the skin and into the bloodstream. An advantage of a transdermal drug delivery route over other types of medication delivery such as oral, topical, intravenous, intramuscular, etc. is that the transdermal patch provides a controlled release of the medication into the patient, usually through either a porous membrane covering a reservoir of medication or through body heat melting thin layers of medication embedded in the adhesive. The main disadvantage to transdermal delivery systems is that the skin is a very effective barrier. As a result, only medications whose molecules are small enough to penetrate the skin can be delivered effectively by this method.

Transdermal patches are designed deliver a specific dose of drug through the skin layers and into the systemic circulation over a period of several hours to days after the application. Generally, a transdermal patch consists of five components: a liner to protect the patch during storage which is removed before application to the skin; a drug reservoir where the drug is contained; a drug release membrane to control drug release from the reservoir through the multi-layers and into skin; a contact adhesive to adhere the patch components to the skin; and a clear backing to protect the patch from outside contamination.

Transdermal patches work very simply in theory. A drug is applied in a relatively high dosage to the inside of a patch, which is worn on the skin for an extended period of time, often 8-10 hours. Through a diffusion process, the drug enters the bloodstream directly through the skin. Since there is high medication concentration on the patch and low concentration in the blood, the drug keeps diffusing into the blood for a long period of time, maintaining the constant concentration of drug in the blood flow. However, this system has its own limitations in which drugs that require high blood levels cannot be administered and may even cause irritation or sensitization of the skin, the adhesives may not adhere well to all types of skin, and the patches may be uncomfortable to wear. Additionally, a new patch must be applied every time a dose of medication is required.

Passive transdermal patch drug delivery systems are those that rely only on natural diffusion to transfer drug from the patch to the skin and into the body. They provide a consistent diffusion rate, depending upon the characteristics of the skin and the design of the patch. Active transdermal patch drug delivery systems are those that use a specific method to aid in the transfer of drug to the skin and into the body. These methods include chemical enhancers and permeators, physical aids like micro-needles, and low electrical current.

Accordingly, there is a great need for a transdermal delivery system that can penetrate the skin and deliver medicine in specific dosages over time. There is also a need for a way for to enable different dosages of medication to penetrate the bloodstream at different times. Similarly, there is a need for a system that can deliver an entire month's worth of medication to the bloodstream with a simple application. There is also a need for a system that can deliver a month's worth of vitamins and micronutrients to the bloodstream with a simple application. Further, there is a need for a replacement for standard methods of medication taking, ensuring those who have trouble remembering to take medicine can have it automatically delivered after a single application.

In this manner, the improved transdermal delivery system of the present invention accomplishes all of the forgoing objectives, thereby providing an easy solution for allowing medications to be delivered through the skin in specific dosages over time. A primary feature of the present invention is a transdermal system for enabling different dosages of medication to penetrate the bloodstream at different times. The present invention can deliver an entire month's worth of medication, vitamins, or micronutrients to the bloodstream with a simple application. Finally, the improved transdermal delivery system of the present invention is capable of replacing oral or injectable routs of entry into the body.

SUMMARY

The following presents a simplified summary in order to provide a basic understanding of some aspects of the disclosed innovation. This summary is not an extensive overview, and it is not intended to identify key/critical elements or to delineate the scope thereof. Its sole purpose is to present some concepts in a simplified form as a prelude to the more detailed description that is presented later.

The subject matter disclosed and claimed herein, in one embodiment thereof, comprises a transdermal delivery system. The transdermal delivery system is intended to be able to store up to a month's worth of a dose of a drug, a vitamin, or other micronutrients. The transdermal delivery system is configured to then deliver the dose of the drug, vitamins, or other micronutrients through a single transdermal application of approximately ten hours or less.

The transdermal delivery system comprises an adhesive bandage and an adhesive layer. The transdermal delivery system may be configured as a transdermal delivery patch. The adhesive bandage may be constructed from a woven fabric, a plastic, or a latex sheet. The adhesive layer covers at least a portion of an inner surface of the adhesive bandage. An outer surface of the adhesive bandage may be water resistant or waterproof.

The transdermal delivery system further comprises a concealed membrane and a barrier layer. The concealed membrane is positional along the inner surface of the adhesive bandage. The barrier layer is a layer of material that separates the concealed membrane from the adhesive bandage. The barrier layer may be adhered to the inner surface of the adhesive bandage by the adhesive layer or by friction.

The transdermal delivery system further comprises a plurality of transdermal delivery capsules. The plurality of transdermal delivery capsules are positional within or otherwise embedded within the concealed membrane. The plurality of transdermal delivery capsules are microscopic capsules and are typically spherical in shape. Each of the plurality of transdermal delivery capsules are manufactured from a bioactive glass material. The bioactive glass spheres are skin absorbent.

The plurality of transdermal delivery capsules are manufactured in varying thicknesses and diameters. Each set of transdermal delivery capsules with the same thickness and diameter react with water in the bloodstream to break down at approximately the same rate. There may be up to thirty or more sets of transdermal delivery capsules, each set with the same thicknesses and diameters. Each set of transdermal delivery capsules are configured to break down in approximately increasing 24 hour intervals as the thicknesses and diameters increase.

The plurality of transdermal delivery capsules are configured to contain or absorb the drug, vitamins, or other micronutrients. The transdermal delivery capsules move out of the concealed membrane and are absorbed through the skin upon skin contact in approximately ten hours or less. As each set of transdermal delivery capsules are of increasing diameter and thickness designed to break down at approximately 24 hour intervals, the transdermal delivery system provides up to a month's worth of daily doses of the drug, vitamins, or other micronutrients for delivery through a single application of the transdermal delivery system to the skin in approximately ten hours or less.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and is intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which:

FIG. 1 illustrates a perspective view of one potential embodiment of a transdermal delivery system of the present invention for delivering medication, vitamins, or micronutrients through the skin and into the bloodstream in specific doses over time in accordance with the disclosed architecture.

FIG. 2 illustrates a cutaway perspective view of one potential embodiment of the transdermal delivery system of the present invention positioned on the skin delivering medication, vitamins, or micronutrients through the skin and into the bloodstream in specific doses over time in accordance with the disclosed architecture.

FIG. 3 illustrates a perspective view of one potential embodiment of the transdermal delivery system of the present invention positioned on the skin delivering medication, vitamins, or micronutrients through the skin and into the bloodstream in specific doses over time in accordance with the disclosed architecture.

FIG. 4 illustrates a exploded close up view of a barrier layer and a plurality of dosing capsules of one potential embodiment of the transdermal delivery system of the present invention for delivering medication, vitamins, or micronutrients through the skin and into the bloodstream in specific doses over time in accordance with the disclosed architecture.

FIG. 5 illustrates a diagrammatic view of the plurality of dosing capsules of one potential embodiment of the transdermal delivery system of the present invention for delivering medication, vitamins, or micronutrients through the skin and into the bloodstream in specific doses over time in accordance with the disclosed architecture.

FIG. 6 illustrates a diagrammatic view of the plurality of dosing capsules of one potential embodiment of the transdermal delivery system of the present invention for delivering medication, vitamins, or micronutrients through the skin and into the bloodstream in specific doses over time in accordance with the disclosed architecture.

DETAILED DESCRIPTION

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof.

Various embodiments are discussed hereinafter. It should be noted that the figures are described only to facilitate the description of the embodiments. They do not intend as an exhaustive description of the invention or do not limit the scope of the invention. Additionally, an illustrated embodiment need not have all the aspects or advantages shown. Thus, in other embodiments, any of the features described herein from different embodiments may be combined.

The present invention, in one exemplary embodiment, is a modified, unique drug delivery system or apparatus. The system or apparatus is comprised of a band-aid-like or transdermal patch-like unit featuring a concealed membrane that houses a plurality of microscopic sphere-like capsules that penetrate the skin to deliver medicine in specific dosages over time. The capsules are preferably comprised of a bio-active glass, in which each capsule varies in thickness to allow different dosages of medicine to penetrate the bloodstream of the user through their skin over time.

Each capsule is configured to hold a specific type of medication, vitamins, or other micronutrients, and each of the capsules have a different thickness (up to 30 different thicknesses or more). After all the capsules are done penetrating through the skin, they become present in the bloodstream. After one day the thinnest capsule will dissolve allowing one day's worth of the drug present in the bloodstream, then after two days the next thickest will dissolve and them process will go like this for approximately 30 days. So, in conclusion, after wearing the patch for a prescribed length of time, such as 8-10 hours, users will have approximately a month's worth of medication penetrated through the skin and that will slowly be released from each of the capsules as the days go on.

Bioactive or bio-glasses are a group of surface reactive glass-ceramic biomaterials. The biocompatibility and bioactivity of these glasses has led them to be used as implant devices in the human body to repair and replace diseased or damaged bones. Most bioactive glasses are silicate based glasses that are degradable in body fluids and can act as a vehicle for delivering ions beneficial for healing.

In a known application, bioglass works through surface reactions once inserted into the body, which promote the healing of tissues in the body, and eventually dissolve completely leaving only tissue where the graft once was. The first step is the exchange of alkali ions, like sodium and calcium, on the surface of the glass with the hydrogen ions of the surrounding bodily fluids. This results in a reaction called hydrolysis, which breaks down the $SiO_2$ compounds on the glass, increasing the pH of the surrounding bodily fluids.

An increased OH— concentration on the surface of the glass continues to break the bonds between silicon and oxygen, forming orthosilicic acid, or $Si(OH)_4$, and silanols on the material surface. The silanol groups then re-polymerise to form a silica gel layer on the surface of the bio-glass, which attracts calcium and phosphate. The calcium and phosphate on the surface of the glass crystalize with the surrounding bodily fluids, creating a mixed carbonated hydroxyapatite (HCA), which is a key component of bone and tooth enamel. The development of this technology has helped to heal bone and other tissue without the need for bone grafting, which eliminates the need for multiple surgeries and reduces complications such as infection, morbidity, and pain.

One challenge of using bio-glasses for drug delivery is associated with their degradable nature in biological environments. The biodegradation of glass depends on its composition, as well as environmental pH, which directly affects the amount of drug released. Delivering protein through the skin by transdermal patches is extremely difficult due to the presence of the stratum corneum which restricts the application to lipophilic drugs with relatively low molecular weight. To overcome these limitations in the past, microneedle patches, consisting of micro/miniature-sized needles have been used to perforate the stratum corneum and to release drugs and proteins into the dermis following a non-invasive route. However, a bio-glass delivery method that would not physically damage the skin would be preferable.

The transdermal delivery system of the present invention is designed for the transdermal delivery of a daily dose of drugs, vitamins, or micronutrients over a time interval of up to one month in a single application of approximately ten hours or less. The transdermal delivery system employs a plurality of varying diameter bioactive glass capsules configured to react with water in the bloodstream to break down and release a contained dose of a drug, vitamin, or other micronutrients. The bioactive glass capsules are configured to contain the drugs, vitamins, or micronutrients.

Figure 2:
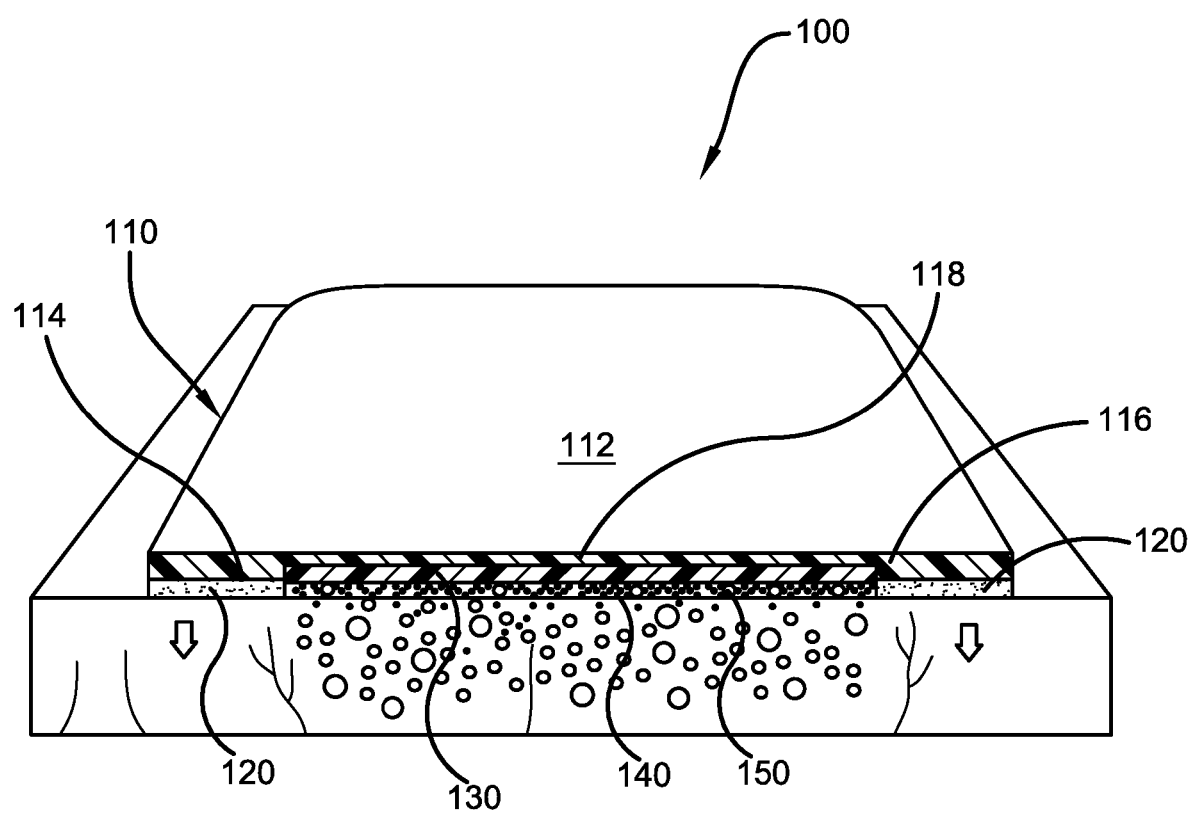

Referring initially to the drawings, FIGS. 1-4 illustrate a transdermal delivery system 100. The transdermal delivery system 100 comprises an adhesive bandage 110 and an adhesive layer 120. The transdermal delivery system 100 may be configured as a transdermal delivery patch constructed as a strip or sheet. The adhesive bandage 110 may be constructed similar to a band-aid or transdermal patch from a woven fabric, latex, or a plastic, such as PVC, polyethylene, polyurethane, or the like. As illustrated in FIG. 2, the adhesive bandage 110 comprises an outer surface 112 and an inner surface 114. The outer surface 112 of the adhesive bandage 110 may be water resistant or waterproof, or even configured to act as an occlusive dressing. The inner surface 114 comprises a perimeter portion 116 and a central portion 118

The adhesive layer 120 may be an acrylate, methyl acrylate, epoxy diacrylate, or any other similar skin-friendly dermal adhesive material layer that covers at least a portion of the inner surface 114 of the adhesive bandage. The adhesive layer 120 may cover the entire inner surface 114. Alternatively, the adhesive layer 120 may cover only the perimeter portion 116 of the inner surface 114. The adhesive layer 120 is configured to hold the transdermal delivery system 100 in place on the skin of the user for at least ten hours.

Figure 4:
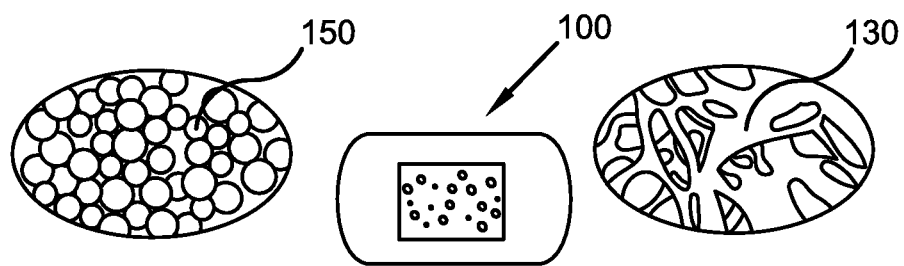

The transdermal delivery system 100 further comprises a concealed membrane 140 and a barrier layer 130. The concealed membrane 140 is positional along and adjacent to the inner surface 114 of the adhesive bandage 110. The concealed membrane 140 is typically centered to cover a central portion 118 of the inner surface 114. The concealed membrane 140 may be a porous membrane or a reservoir membrane. The barrier layer 130 is a layer of material that separates the concealed membrane 140 from the adhesive bandage 110. The barrier layer 130 may be a plastic layer, such as a polyethylene sheet or similar material, designed to separate the other layers of the transdermal delivery system 100 as illustrated in FIG. 4. The barrier layer 130 may be adhered to the inner surface 114 of the adhesive bandage 110 by the adhesive layer 120 or by friction.

The transdermal delivery system 100 may further comprise a release liner 160. The release liner 160 is a protective sheet or cover that protects the adhesive layer 120 and the concealed membrane 140 from contamination until use. The user simply peals back and removes the release liner 160 exposing the adhesive layer 120 and the concealed membrane 140 just prior to use as illustrated in FIG. 1.

Figure 3:
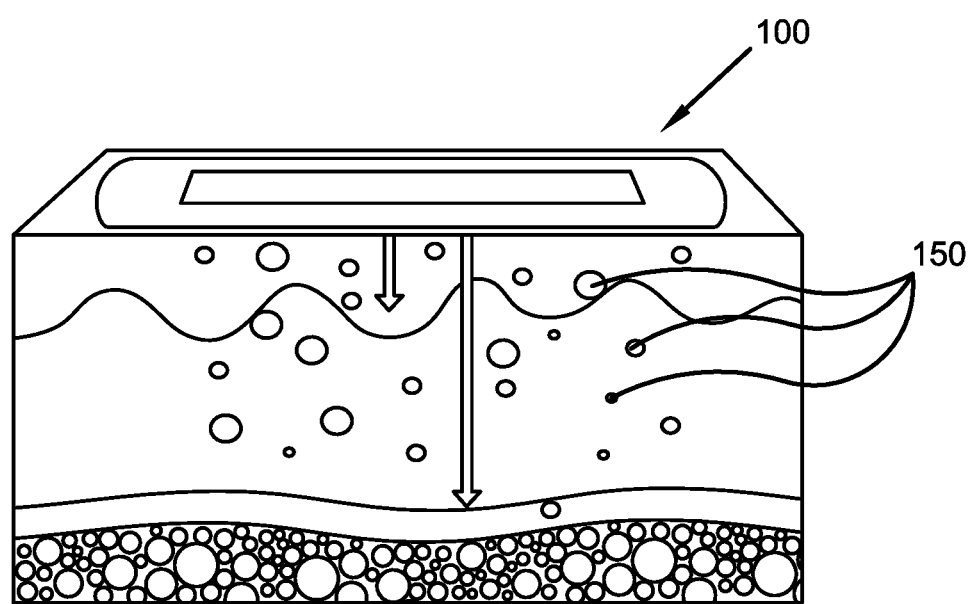

As further illustrated in FIG. 4, the transdermal delivery system 100 further comprises a plurality of transdermal delivery capsules 150. The plurality of transdermal delivery capsules 150 are positional within or otherwise embedded within the concealed membrane 140 during manufacturing. The plurality of transdermal delivery capsules 150 are microscopic capsules that are typically spherical in shape. Each of the plurality of transdermal delivery capsules 150 are manufactured from a bioactive material, such as a bioglass material forming bioactive glass spheres. Typically, each transdermal delivery capsules 150 is constructed from some combination of silicon dioxide, sodium dioxide calcium oxide, or phosphorus. As illustrated in FIGS. 2 and 3, the bioactive glass spheres are skin absorbent over time.

The plurality of transdermal delivery capsules 150 are manufactured in varying thicknesses and diameters. As illustrated in FIG. 3, each set of transdermal delivery capsules 150 with the same thickness or diameter react with water in the bloodstream to break down at approximately the same rate. There may be up to thirty or more sets of transdermal delivery capsules 150, each set with the same thicknesses or diameters. Each set of transdermal delivery capsules 150 are configured to break down in approximately increasing 24 hour intervals as the thicknesses or diameters increase. The specific number of transdermal delivery capsules 150 is dependent on the amount of drug that needs to be delivered per day and the number of days the transdermal delivery system 100 is good for. The transdermal delivery system 100 is typically good for between one and thirty days or more.

The plurality of transdermal delivery capsules 150 are configured to contain or absorb the drug, vitamins, or other micronutrients. A single application of the transdermal delivery system 100 through skin contact is typically approximately ten hours or less. As such, the transdermal delivery capsules 150 move out of the concealed membrane and are absorbed through the skin upon skin contact in that timeframe. As each set of transdermal delivery capsules 150 are of increasing diameter and thickness designed to break down at approximately 24 hour intervals, the transdermal delivery system 100 provides up to a month's worth of daily doses of the drug, vitamins, or other micronutrients for delivery through a single application of the transdermal delivery system 100 to the skin in approximately ten hours or less. The thirty day dose of a drug, a vitamin, or a micronutrient is delivered in 28 to 31 approximately equal daily doses depending on the particular month.

When the transdermal delivery system 100 is applied to the skin, the bioactive glass spheres 150 absorb through the layers of skin. This typically occurs over up to a ten hour interval but may be longer as needed. Once absorbed, the thinnest shelled bioactive glass spheres 150 will react with $H_2O$ in the blood to form Si—OH. After a complete unit of $SiO_2$ breaks down, it forms $Si(OH)_4$ which is then released into the bloodstream. Subsequently, the drug, vitamins, or other nutrients that were contained within the thickness of the bioactive glass sphere 150 are released directly into the bloodstream. This process is repeated with each set of differently sized bioactive glass spheres 150 in chronological form from thinnest to thickest. As there may be thirty or more different sets of thicknesses for the differently sized bioactive glass spheres 150, each transdermal delivery system 100 or patch will provide a continuous flow of the drug, vitamins, or other nutrients for up to a month through a single application of the transdermal delivery system 100.

Figure 5:
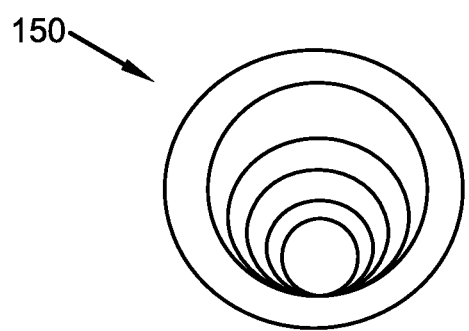
Figure 6:
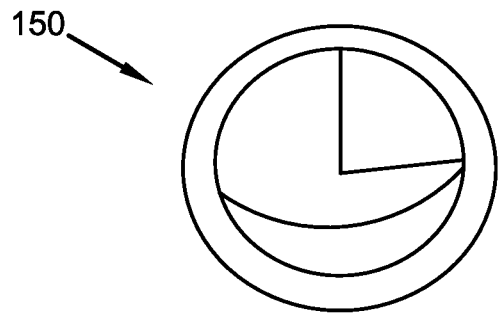

FIGS. 5 and 6 illustrates an example of an absorbency sphere. As the sphere becomes larger, the time interval to release the contents increases proportionally. FIG. 5 illustrates a diagram of how each bioactive glass sphere 150 absorbs contents 170 (the drug, vitamins, or other nutrients). To find dr/dt where r=3.5 µm and the rate of emission=dv/dt=0.001 microliters per hour, use the volume of a sphere formula v=(4/3) (Π) (r3) and manipulate the equation by taking the derivative using the power rule $$\frac{dv}{dt} = (4)(\pi)(r^2)\left(\frac{dr}{dt}\right).$$

By plugging in the given conditions and variables:

$$0.001 = (4)(\prod)((3.5)^2)\left(\frac{dr}{dt}\right).$$

Solving for dr/dt provides 0.0000065 microns per hour. In other words, the radius is increasing at a steady rate of 0.0000065 microns per hour. This is advantageous as though the bioglass does not need to be spherical, the shape may be optimized depending on the hourly rate that the drug needs to be given. This also allows for customization for each patient's needs.

As illustrated in FIG. 6, the glass shell 152 is referred to as v. To find dr/dt where r2=3 µm; $dr^2/dt$=−0.116667; r1=3 µm; and dr1/dt=0, subtract the volume of a bigger sphere by reducing it by the volume of the smaller sphere to get the value of "v" or V=$((4/3)(\pi)(r2)^3)-((4/3)(\pi)(r1)^3)$. Using the power rule to find the derivative with respect to time, $$dv/dt = \left((4)(\pi)(r2)^2)\left(\frac{dr2}{dt}\right)\right) - \left((4)(\pi)(r1)^2\left(\frac{dr1}{dt}\right)\right).$$

By plugging in the given conditions to find that 'v' decreases in respect to time, $$\frac{dv}{dt} = ((4)(\pi)(3)^2(-0.116667)) - ((4)(\pi)(3)^2(0))$$

so that dv/dt=−13.1947 microliters in volume per day.

Notwithstanding the forgoing, the transdermal delivery system 100 can be any suitable size, shape, and configuration as is known in the art without affecting the overall concept of the invention, provided that it accomplishes the above stated objectives. One of ordinary skill in the art will appreciate that the shape and size of the transdermal delivery system 100 and its various components, as show in the FIGS. are for illustrative purposes only, and that many other shapes and sizes of the transdermal delivery system 100 are well within the scope of the present disclosure. Although dimensions of the transdermal delivery system 100 and its components (i.e., length, width, and height) are important design parameters for good performance, the transdermal delivery system 100 and its various components may be any shape or size that ensures optimal performance during use and/or that suits user need and/or preference. As such, the transdermal delivery system 100 may be comprised of sizing/shaping that is appropriate and specific in regard to whatever the transdermal delivery system 100 is designed to be applied.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A transdermal delivery system comprising:
   an adhesive bandage portion;
   an adhesive layer covering at least a part of an inner surface of the adhesive bandage portion;
   a porous membrane positional along a central part of the inner surface of the adhesive bandage portion;
   a polyethylene barrier layer separating the adhesive bandage portion and the porous membrane; and a plurality of bioactive glass transdermal delivery positional within the porous membrane; and
      wherein the plurality of bioactive glass transdermal delivery capsules comprising a drug, a vitamin, or a micronutrient;
      wherein the plurality of bioactive glass transdermal delivery capsules comprise a first set of capsules each comprising a first capsule wall thickness, a second set of capsules each comprising a second capsule wall thickness, and a third set of capsules each comprising a third capsule wall thickness;
      wherein the plurality of bioactive glass transdermal capsules are absorbed into skin upon single application of the transdermal delivery system to the skin for about 10 hours;
      wherein the second capsule wall thicknesses are calculated to react with water from bloodstream to release the drug, vitamin, or micronutrient approximately 24 hours after the first capsule wall thicknesses react with water from bloodstream to release the drug, vitamin, or micronutrient within the first set of capsules; and
      wherein the third capsule wall thicknesses are calculated to react with water from bloodstream to release the drug, vitamin, or micronutrient approximately 24 hours after the second capsule wall thicknesses react with water from bloodstream to release the drug, vitamin, or micronutrient within the second set of capsules.

2. The transdermal delivery system of claim 1 further comprising a release liner configured to protect the adhesive layer and the porous membrane until use.

* * * * *